United States Patent [19]

Lindley

[11] Patent Number: 4,739,034
[45] Date of Patent: Apr. 19, 1988

[54] POLYAMIDE FROM BIS (BIPHENYL-2,2'-DICARBOXYLIMIDE)

[75] Inventor: Andrew A. Lindley, Frodsham, United Kingdom

[73] Assignee: Imperial Chemical Industries PLC, London, England

[21] Appl. No.: 865,020

[22] Filed: May 20, 1986

[30] Foreign Application Priority Data

May 20, 1985 [GB] United Kingdom ................. 8512683

[51] Int. Cl.[4] .............................................. C08G 69/00
[52] U.S. Cl. .................................. 528/322; 428/473.5; 428/474.4; 524/606; 528/321
[58] Field of Search ................ 528/322, 321; 524/606; 428/473.5, 474.4

[56] References Cited

U.S. PATENT DOCUMENTS 4,346,212  8/1982  Robinson et al. ................... 528/353

Primary Examiner—Harold D. Anderson
Attorney, Agent, or Firm—Cushman, Darby & Cushman

[57] ABSTRACT

Polyamides containing in-chain aromatic groups, particularly diphenyl groups. Such polyamides may be prepared by reacting an alpha-omega-hydrocarbyl bis(-biphenyl-2,2[1]-dicarboxylmide) with a diamine and are useful as the matrix in fibre-reinforced composites.

14 Claims, No Drawings

POLYAMIDE FROM BIS (BIPHENYL-2,2'-DICARBOXYLIMIDE)

The present invention relates to substantially linear polyamides, particularly to polyamides containing in-chain residues derived from automatic dicarboxylic acids, and to the preparation thereof.

The preparation of polyamides from aromatic dicarboxylic acids often involves use of the expensive acid chloride thereof and a suitable solvent. Evolution of hydrogen chloride during the polymerisation renders the reaction unsuitable for use in the hand lay-up of fibre reinforced composites and reaction injection moulding.

Hydrocarbyl bis-maleimides are known to react with aliphatic diamines to give a mixture of ill-defined products. It is known that where hydrocarbyl bis-maleimides are reacted with aromatic diamines reaction occurs at the carbon-carbon double bond of the maleimide groups and polymers having in-chain imide groups are formed.

We have now found that certain alpha, omega-hydrocarbyl bis(biphenyl-2,2'-dicarboxylimides) as hereinafter defined can be reacted with certain diamines to form polyamides.

Accordingly, a first aspect of the present invention provides substantially linear polyamides comprising repeating units of the general formula:

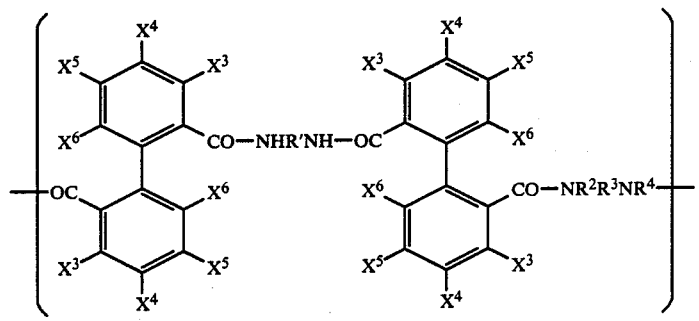

wherein
$R^1$ and $R^3$, which may be the same or different, are divalent organic groups;

$R^2$ and $R^4$, which may be the same or different, are hydrogen or lower alkyl groups having up to 5 carbon atoms; and $X^3$, $X^4$, $X^5$ and $X^6$, each of which may be the same or different, are hydrogen or substituents which do not adversely affect (i) the properties of the polyamides according to the first aspect of the present invention or, (ii) the preparation thereof by the process according to the second aspect of the present invention.

Within the scope of the term divalent organic group are included divalent hydrocarbyl groups, which may be linear or branched alkyl, aryl, akaryl, or aralkyl; and divalent hydrocarbyl groups which are substituted with one or more in-chain or pendant hetero-atoms which hetero-atoms do not react with imide groups. Examples of suitable in-chain hetero-atoms include inter alia O and S and combinations thereof. Examples of suitable pendant hetero-atoms include inter alia halogen, e.g. chlorine.

Examples of divalent hydrocarbyl groups include inter alia $-(CH_2)-_n$, where n is an integer, e.g. 2, or 6; phenylene; xylylene; and di-phenylene-methane.

Examples of divalent hydrocarbyl groups which are substituted with one or more in-chain hetero-atoms include inter alia $-(CHR^5CHR^5O)_mCH_2CH_2-$, where m is an integer, e.g. 48, and $R^5$ is H or methyl except that both $R^5$'s are not methyl; $-(CH_2)_5-O-(CH_2)_5$; $-(\phi-X-\phi)p$ where, $\phi$ is the phenylene group, X, each of which may be the same or different, represents $-O-$, $-SO_2$, $-CONH-$, $-CO-$, and p is an integer from 0 to 15.

Where high temperature stability or a high Tg is required in polymers of the general formula I $R^1$ and $R^3$ are preferably aromatic groups. Most preferably $R^1$ and $R^3$ are chains of aromatic groups containing in-chain carbon or hetero-atoms, e.g. $-O-$ and $-SO_2-$; the aforesaid chains confer additional desirable properties, e.g. solvent properties and softening point; $R^2$ and $R^4$ are preferably hydrogen.

Preferably $X^6$ is hydrogen, most preferably $X^3$ and $X^6$ are separately hydrogen and more particularly preferably $X^3$, $X^4$, $X^5$ and $X^6$ are separately hydrogen. Where $X^3$, $X^4$, $X^5$ or $X^6$ are substituents, examples thereof include inter alia lower alkyl groups, e.g. methyl, or halo groups, e.g. chloro; we do not exclude the possibility that where two of the aforesaid $X^3$, $X^4$, $X^5$ and $X^6$ are substituents such substituents may join to form a further ring which may be aromatic or alicyclic.

Where $X^6$ are not hydrogen it may be chosen such that it facilitates or hinders rotation about the phenylene-phenylene bond.

A second aspect of the present invention provides a process for the preparation of polyamides of the general formula I by reacting under suitable conditions a bis-imide of the general formula:

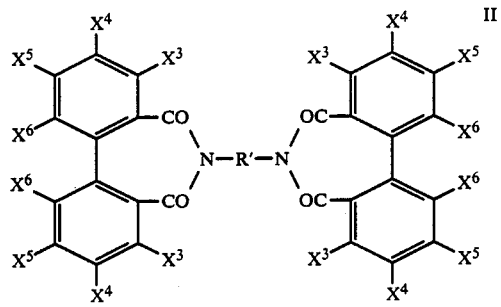

wherein $R^1$, $X^3$, $X^4$, $X^5$ and $X^6$ have the meanings hereinbefore ascribed to them with a diamine of the general formula $$NHR^2-R^3-NHR^4 \qquad \text{III}$$

wherein $R^2$, $R^3$ and $R^4$ have the meanings hereinbefore ascribed to them with the proviso that $R^2$, $R^3$ or $R^4$ does not bear a substituent which reacts with the imide groups in II; preferably $R^2$ and $R^4$ are separately hydrogen.

Where $R^3$ in the diamine of the general formula III represents an alkyl chain, which may be substituted, e.g. with in-chain or pendant atoms or groups, or unsubstituted, it is preferred that the α, ω groups are methylene groups. It is preferred that $R^1$ is aromatic since this increases the reactivity of the imide group and enhances the ring opening reactivity thereof and hence increases the rate of polymerisation. Further it has been found that the rate of polymerisation tends to be proportional to the $pK_b$ of the diamine which is reacted with the diimide; thus, an aliphatic diamine, e.g. $NH_2(CH_2)_6NH_2$, reacts faster than an aromatic diamine, e.g. $NH_2ArCH_2ArNH_2$, which in turn reacts faster than an aromatic diamine which bears a substituent which lowers the $pK_b$ of the amino group, e.g. $NH_2Ar\text{-}SO_2ArNH_2$. Accordingly, where a rapid reaction is required in the process of the present invention it is preferred to use a diamine of the general formula III in which $R^3$ is an alkyl group having up to 20 carbon atoms and $R^2$ and $R^4$ are hydrogen.

We do not exclude the possibility that catalysts and/or inhibitors may be used the process according to the second aspect of the present invention.

The process according to the present invention is preferably carried out by reacting neat bis-imide of the general formula II with neat diamine of the general formula III, typically in a molar ratio of about 1:1, although we do not exclude the possibility that the reaction may be carried out in the presence of a suitable inert diluent, e.g. methylene chloride.

The process according to the present invention is preferably carried out in the temperature range 20° C. to 200° C.

Where it is desired that any of $X^3$, $X^4$, $X^5$ or $X^6$ are substituent groups we do not exclude the possibility that such substituents may be introduced into the polyamide of the first aspect of the present invention after it has been prepared.

A third aspect of the present invention provides bis-imides of the general formula II.

The bis-imide of the general formula II, where $X^3$, $X^4$, $X^5$ and $X^6$ are separately hydrogen, for use in the process of the present invention may be prepared by reacting 2,2'-biphenyldicarboxylic anhydride with a diamine of the general formula:

$$NH_2-R^1-NH_2 \qquad \text{IV}$$

wherein $R^1$ has the meaning hereinbefore ascribed to it. It will be appreciated that where $X^6$ is a substituent it may, for example because of steric affects, retard or preclude the formation of bis-imides of general formula II.

In the preparation of a bis-imide of the general formula II, typically, the diamine of the general formula IV is reacted with a solution, preferably a non-aqueous solution, and more preferably a solution in a polar aprotic solvent of 2,2'-biphenyldicarboxylic anhydride. The reaction may be carried out at a temperature in the range 0° C. to 150° C. Conveniently, the anhydride, preferably neat, is added to a solution of the diamine in a suitable solvent. It will be appreciated that the reaction is a two step reaction. In the first step the anhydride rings are opened to generate a diamine. In the second step cyclisation occurs with elimination of water. The second step is preferably carried out in the presence of a suitable dehydrating agent, for example an anhydride, e.g. acetic anhydride, and a weak base, e.g. sodium acetate. The first step is preferably carried out at between 0° C. and 20° C. and the second step is preferably carried out between 100° C. and 150° C. We do not exclude the possibility that the second step may be carried out as a melt.

The polyamides of the present invention may be used as the matrices for fibre-reinforced composites. In such composites, suitable fibre reinforcing materials include, for example, glass, e.g. in the form of mat, tapes, continuous fibre or chopped rovings; inorganic mineral fibres; or preferably fibres of suitable high temperature resistant organic fibres, e.g. a poly aromatic amide, e.g. Kevlar (RTM); or more preferably carbon fibre.

Where a polyamide according to the present invention is used as a matrix for a fibre-reinforced composite, such a composite may be produced for example by placing fibres, for example carbon fibres, in a mould of a desired shape and impregnating the fibres with a mixture of a bis-imide of the general formula II with a diamine of the general formula III. The fibres and the aforesaid mixture are heated to an appropriate temperature, e.g. 200° C.–300° C., often at a pressure of about 200 psi, for typically about 7 hours, to form a fibre-reinforced composite.

Where the aforesaid mixture is a solid or is very viscous, and is thus not sufficiently fluid for satisfactory impregnation of the fibres, the mixture may be diluted with, e.g. dissolved in, a low boiling solvent, e.g. methylene chloride, in order to provide a mixture of the desired fluidity. The low boiling solvent may be caused or allowed to evaporate before the reaction of the bis-imide of the general formula II with the diamine of the general formula III is initiated. Alternatively, the imide and amine may be partially reacted to give a "B-stage" mixture, the fibres are then impregnated with this mixture which is then fully cured.

The polyamides of the present invention may be prepared in reaction injection moulding processes to provide shaped articles. In such processes, moulding is typically effected at a moulding temperature in the range 100° C. to 300° C. and a pressure of 10 to 20 megapascales. In such processes the bis-imide of general formula II and the diamine of general formula III are preferably injected into the mould separately and simultaneously.

The polyamides of the present invention may include inter alia heat and light stabilisers, antioxidants, colouring pigments and particulate filler materials, e.g. chalk, calcium carbonate, talc, mica, carbon black and glass.

The present invention will be further illustrated with reference to the following Examples.

EXAMPLE 1

This Example illustrates the preparation of a bis(-biphenyl-2,2'-dicarboxylimide) according to the third aspect of the present invention.

2,2'-Biphenyl dicarboxylic anhydride (9.3 g, 0.042 moles) was added as a solid, to a cooled (0°–15° C.), stirred solution of 4,4'-diaminodiphenyl methane (4.1 g, 0.021 moles) in dry N,N-dimethylacetamide (30 ml), over a period of 1.5 hours. The mixture was warmed to room temperature and stirred for 1 hour, acetic anhydride (4.7 g, 0.046 moles) and triethylamine (0.4 g, 0.004 moles) were added and the mixture was stirred for a further 4 hours. A small sample of the mixture was added to water; infra-red spectroscopy on the sample of product isolated therefrom indicated incomplete reaction. A further portion of acetic anhydride (10 ml), dry sodium acetate (c.a. 4 g), and N,N-dimethylacetamide (20 ml) were added to the mixture and it was heated to 80° C. for 1 hour. The mixture was allowed to stand overnight and was then added to water. The pink solid which precipitated was filtered, washed with water, then with industrial methylated spirit (IMS) and was then boiled with IMS (in which the solid is mainly insoluble). The solid was further extracted with a 50:50 acetonitrile:ethanol mixture and a white solid (10.2 g) was left. Gel permeation chromatography of the white solid in chloroform indicated the presence of one component. The infra-red spectrum and elemental analysis (Found: C, 79.95; H, 3.91; N, 4.36; calculated for $C_{41}H_{26}N_2O_4$: C, 80.64; H, 4.29; N, 4.59) of the white solid were consistent with those of 4,4′-bis-(diphenyl-2,2′-dicarboxylimide)-diphenylmethane.

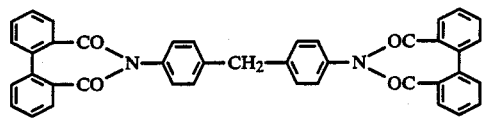

EXAMPLE 2

This example illustrates the preparation of a second bis(biphenyl-2,2′-dicarboxylimide) according to the third aspect of the present invention.

4,4′-bis-(4-aminophenoxy)-diphenylsulphone (10.4 g, 0.024 moles) was dissolved in sieve-dried N,N-dimethylacetamide (60 ml) and the solution was cooled to 5° C. To this solution, solid 2,2′-biphenyldicarbocylic anhydride (12 g, 0.054 moles) was added, whilst the temperature of the solution was kept below 15° C. until the addition was complete (45 min). The solution was allowed to warm to room temperature overnight, and was then heated to 80° C. for 1 hour to ensure complete reaction. The reaction mixture was cooled to room temperature, acetic anhydride (40 ml) and sodium acetate (6 g) were added and the mixture was heated to 80° C. for 6 hours. On cooling the mixture was poured into water (600 ml), the solid thus formed was filtered, washed with water, then with IMS, and then boiled with IMS (in which it is insoluble), to leave a pale brown powder (20 g).

Gel permeation chromatography, infra-red analysis and elemental analysis (Found; C, 73.49; H, 3.64; N, 3.23; S, 4.08. Calculated for $C_{25}H_{32}N_2O_8S$: C, 73.93; H, 3.79; N, 3.32; S, 3.79) indicated that the pale brown solid was 4,4′-bis-[4-(diphenyl-2,2′-dicarboxylimido)-phenoxy]diphenylsulphone.

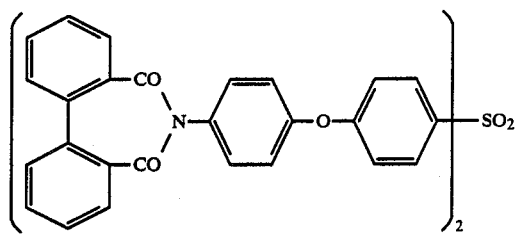

EXAMPLE 3

This example illustrates the preparation of a third bis(biphenyl-2,2′-dicarboxylimide) according to the third aspect of the present invention.

Diphenic anhydride (8.96 grams) was added portionwise, as a solid, over 1.5 hours to a solution, cooled to 4° C., of 4,4′-diaminodiphenylsulphone (4.96 grams; dried at 60° C. under vacuum for 1 hour) in N,N-dimethylacetamide (80 mls; dried over 5A molecular sieve); during the addition the temperature of the solution was allowed to rise slowly to 20° C. The temperature of the reaction mixture was then raised to 65° C., a clear solution formed, and was then held at 50° C. for 1 hour. The reaction mixture was then allowed to stand overnight at room temperature.

Triethylamne (2 mls) and then acetic anhydride (25 mls) were added to the reaction mixture which was warmed to 70° C. and allowed to stand for 1 hour. On cooling, the solution gave a precipitate which was filtered, washed with water and then methanol, and then dried under vacuum at 60° C. for 2 hours to afford a product (6.5 grams). The product was crystallised from boiling dimethylacetamide and yielded a white crystalline material, m.p. 314°–319° C., the mass spectrum of which was consistent that a diimide of the structure

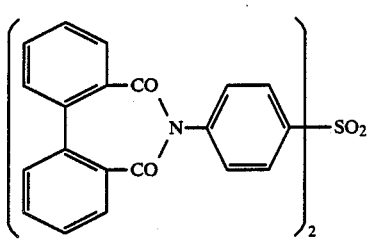

EXAMPLES 4–17

These examples illustrate the preparation of polyamides according to the first aspect of the present invention.

General Method

A mixture of a bis-imide and a diamine, as a powder (prepared by mixing the neat components or by dissolving the components in methylene chloride and evaporating) or as a solution in methylene chloride or dried N,N-dimethylacetamide (DMA) was treated at a specific temperature for a specified time. Where the polymerisation reaction was carried out in DMA the reaction mixture was poured into water, the product was isolated by filtration, washed with water (3X) and dried under vacuum at, e.g. 70° C. Where the polymerisation reaction was carried out in methylene chloride the product was recovered by evaporating off the solvent. Details of the reaction conditions are given in Table 1.

The amine A used in Examples 8, 9 and 10 was prepared by the following procedure.

4,4'-bis-[diphenyl-2,2'-dicarboxylimido)-phenoxy]-diphenylsulphone (1.62 g) was added to a solution of 1,6-hexamethylene diamine (9 g) in dry DMA (40 ml) and the mixture was warmed and stirred at 90° C. for 1 hour. The mixture was allowed to cool overnight and was then poured into water. The resulting precipitate was filtered, washed with water, and dried under vacuum, to leave an off-white solid (1.44 g), with a melting point of about 180° C. The infra-red spectrum and gel permeation chromatography of the product were consistent with the following structure:

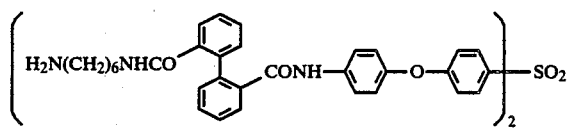

Details of the polyamides prepared in Examples 4 to 17 are given in Tables 2 and 3.

TABLE 2

| Ex No | Gel Permeation Chromatography | | | | T.G.A. (%/°C.) | Glass Transition Temp$^a$ (°C.) | 1% [R.V.] 25°C. |
|---|---|---|---|---|---|---|---|
| | $M_n$ | $M_w$ | $M_z$ | D | | | |
| 4 | 11770 | 15300 | b | 1.3 | 1.95/360 | b | b |
| 5 | 7260 | 11340 | b | 2.0 | b | b | b |
| 6 | 9100 | 13150 | b | 1.4 | b | b | b |
| 7 | 7890 | 15740 | b | 2.0 | b | b | b |
| 8 | 9510 | 66560 | 271000 | 7.0 | 2.2/400 | 183 | b |
| 9 | 8740 | 97200 | 483000 | 11.1 | 1.7/400 | 188 | b |
| 10 | 8640 | 76020 | 371000 | 8.8 | 1.3/400 | 186 | b |
| 11 | 5040 | 9670 | b | 1.9 | b | b | b |
| 12 | 11310 | 15260 | b | 1.3 | b | b | b |
| 13 | 14830 | 18450 | b | 1.2 | 3.44/360 | 237 | b |
| 14 | 17440 | 190600 | 669000 | 10.9 | 1.2/400 | 227 | b |
| 15 | b | b | b | b | b | 79 | 0.16 |
| 16 | b | b | b | b | b | 197 | 0.16 |
| 17 | b | b | b | b | b | 252 | 0.26 |

Gel permeation chromatography in DMA using (i) for Examples 4–7 and 11–13, a 1000 to a 30,000 molecular weight exclusion column, all products are excluding, and (ii) for Examples 8–10 and 14, a 4000 to 1000,000 molecular weight exclusion column.
TGA: Thermogravimetric analysis (dynamic: 20° C. per minute in nitrogen) weight loss % at °C.
a: By differential scanning calorimetry.
b: Not determined.

TABLE 1

| Ex No | Bis-imide Prepared in Ex No | Weight (grams) | Diamine (Weight) in grams | Solvent (mls) | Temp. (°C.) | Time (hrs) | Weight of Product (grams) |
|---|---|---|---|---|---|---|---|
| 4 | 1 | 0.9 | NH$_2$(CH$_2$)$_2$NH$_2$ (0.09) | DMA (4) | 150 | 6 | |
| 5 | 1 | 0.9 | NH$_2$(CH$_2$)$_2$NH$_2$ (0.09) | CH$_2$Cl$_2$ (4) | 20 | 20 | |
| 6 | 2 | 0.22 | NH$_2$(CH$_2$)$_2$NH$_2$ (0.016) | — | 240 | 0.5 | |
| 7 | 2 | 0.22 | NH$_2$(CH$_2$)$_2$NH$_2$ (0.03) | — | 240 | 0.5 | |
| 8 | 2 | 0.96 | A (1.225) | DMA (16) | 150 | 4 | |
| 9 | 2 | 0.96 | A (1.225) | — | 250 | 0.03 | |
| 10 | 2 | 0.96 | A (1.225) | — | 250 | 1 | |
| 11 | 1 | 1.081 | B (0.765) | — | 210 | 5 | |
| 12 | 1 | 1.081 | B (0.765) | — | 240 | 3 | |
| | | | | | 265 | 4 | |
| 13 | 1 | 1.081 | B (0.765) | — | 270 | 7 | |
| 14 | 2 | 1.189 | B (0.609) | — | 260 | 6 | |
| 15 | 1 | 1.016 | NH$_2$(CH$_2$)$_{12}$NH$_2$ (0.33) | DMA (10) | 80 | 5 | 1.2 |
| 16 | 1 | 1.016 | C (0.26) | DMA (10) | 90 | 2 | 1.1 |
| 17 | 1 | 1.52 | D (0.52) | DMA (8) | 150 100 | 0.16 7 | 1.8 |

B: 4,4'-bis-(4-aminophenoxy)-diphenylsulphone.
C: Tri-methylhexamethylene diamine.
D: Bis(4-aminocyclohexyl)methane.

TABLE 3

| | Solvent for polyamide | | | | | | | |
|---|---|---|---|---|---|---|---|---|
| Ex No | Dimethyl Sulphoxide | Dimethyl Acetamide | M$_e$OH/ CHCCl$_3$ (70/30 v/v) | Acetone | Ethyl acetate | CH$_3$OH | CHCl$_3$ | C$_2$H$_5$OH |
| 15 | Yes | Yes | b | No | No | No | No | b |
| 16 | Yes | Yes | b | No | No | No | No | b |
| 17 | Yes | Yes | Yes | No | No | b | No | No | b: Not determined

EXAMPLE 18

A solution of a portion (6.10 grams) of the diimide prepared in Example 1 and 4,4'-diaminodiphenylmethane (1.98 grams) in chloroform (50 mls) was used to impregnate carbon-fibres. The carbon fibre was placed on a Melinex (RTM) film, a portion of the solution was poured onto the films and the solvent was allowed to evaporate; this process was repeated until a pre-preg was obtained which contained about 38% w/w carbon fibre.

A composite (of dimensions 3 cm×1 cm×0.25 cm) was prepared by laying the impregnated fibres onto a mould having the aforesaid dimensions and applying pressure at an initial temperature of 210° C., the temperature was raised in increments over 20 minutes to 260° C. and maintained at this temperature for 25 minutes.

Dynamic Mechanical Analysis on the resulting composite revealed that it had a Youngs Modulus at 20° C. of 8.0 GPa, 7.9 GPa at 100° C. and 7.5 at 200° C.; the peak of the loss process (tan δ) occurred at 270° C.

What is claimed is:

1. A polyamide comprising repeat units of the general formula

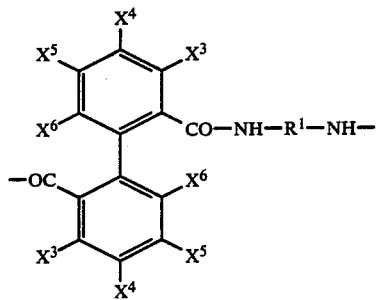

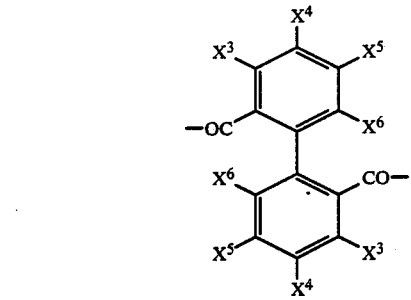

wherein
$R^1$ and $R^3$, which are the same or different, are divalent organic groups;
$R^2$ and $R^4$, which are the same or different, are hydrogen or lower alkyl groups having up to five carbon atoms;
$X^3$, $X^4$, $X^5$ and $X^6$, each of which is the same or different, are hydrogen or groups which do not adversely affect the properties of the polyamide.

2. A polyamide as claimed in claim 1 wherein $R^2$ and $R^4$ are hydrogen.

3. A polyamide as claimed in claim 1 wherein $X^3$, $X^4$, $X^5$ and $X^6$ are hydrogen.

4. A polyamide as claimed in claim 1 wherein $R^1$ and $R^3$ are aromatic residues.

5. A polyamide as claimed in claim 1 wherein $R^1$ and $R^3$ are aromatic groups or chains of aromatic groups containing in-chain hetero-atoms and $R^2$ and $R^4$ are hydrogen.

6. A process for the preparation of polyamide as claimed in claim 1 characterised in that a bis-imide of the general formula

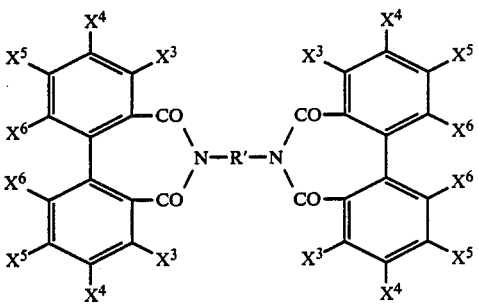

is reacted with a diamine of the general formula

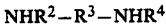

$$NHR^2-R^3-NHR^4$$

wherein $R^1$, $R^2$, $R^3$, $R^4$, $X^3$, $X^4$, $X^5$ and $X^6$ have the meaning ascribed to them in claim 1.

7. A process as claimed in claim 6 wherein neat bis-imide is reacted with neat di-amine.

8. A process as claimed in claim 6 wherein $R^1$ is an aromatic residue, $R^3$ is an alkylene residue and $R^2$ and $R^4$ are hydrogen.

9. A process as claimed in claim 6 wherein reaction is effected at a temperature between 20° C. and 200° C.

10. A process as claimed in claim 6 wherein $R^3$ is an alkylene group having up to 20 carbon atoms and $R^2$ and $R^4$ are hydrogen.

11. A fibre-reinforced composite characterised in that the matrix comprises a polyamide as claimed in claim 1.

12. A process for the preparation of a fibre-reinforced composite as claimed in claim 11, which process comprises the steps of impregnating fibre with, a mixture of a bis-imide as claimed in claim 6 and a diamine as defined in claim 6 and heating fibre and the mixture to an appropriate temperature.

13. A process as claimed in claim 6 carried out under reaction injection moulding conditions.

14. A process as claimed in claim 13 which process comprises injecting a bis-imide as defined in claim 6 and a diamine as defined in claim 6 separately and simultaneously into a mould and moulding the mixture at a temperature of between 100° and 300° C. under a pressure of 10 to 20 megapascales.

* * * * *